US009743915B2

(12) United States Patent
AlMaatouq (10) Patent No.: US 9,743,915 B2
(45) Date of Patent: Aug. 29, 2017

(54) ADVANCED BIOPSY NEEDLE (71) Applicant: Mohamed Abdullah AlMaatouq, Riyadh (SA)

(72) Inventor: Mohamed Abdullah AlMaatouq, Riyadh (SA)

(73) Assignee: King Saud University, Riyadh (SA)

( * ) Notice: Subject to any disclaimer, the term of this patent is extended or adjusted under 35 U.S.C. 154(b) by 94 days.

(21) Appl. No.: 14/527,898

(22) Filed: Oct. 30, 2014

(65) Prior Publication Data
US 2016/0120517 A1    May 5, 2016

(51) Int. Cl.
*A61B 10/02* (2006.01)
*A61M 5/32* (2006.01)

(52) U.S. Cl.
CPC ...... *A61B 10/0275* (2013.01); *A61B 10/0283* (2013.01); *A61M 5/3293* (2013.01); *A61B 2010/0208* (2013.01)

(58) Field of Classification Search
CPC ................. A61B 10/0275; A61B 10/0283
See application file for complete search history.

(56) References Cited

U.S. PATENT DOCUMENTS

| | | | |
|---|---|---|---|
| 4,655,226 A * | 4/1987 | Lee | A61B 10/025 600/567 |
| 5,199,441 A | 4/1993 | Hogle | |
| 6,554,778 B1 * | 4/2003 | Fleming, III | A61B 10/025 600/567 |
| 7,179,232 B2 * | 2/2007 | Sutton | A61B 10/025 600/562 |
| 7,722,549 B2 | 5/2010 | Nakao | |
| 7,794,411 B2 | 9/2010 | Ritchart et al. | |
| 8,167,816 B2 | 5/2012 | Burdorff et al. | |
| 8,187,204 B2 | 5/2012 | Miller et al. | |
| 8,277,393 B2 | 10/2012 | Miller et al. | |
| 8,591,435 B2 | 11/2013 | Ritchart et al. | |
| 8,721,563 B2 | 5/2014 | Taylor et al. | |
| 2003/0236471 A1 * | 12/2003 | Fisher | A61B 10/0266 600/573 |
| 2006/0116605 A1 | 6/2006 | Nakao | |
| 2010/0030108 A1 * | 2/2010 | Anderson | A61B 10/0275 600/567 |
| 2011/0098596 A1 | 4/2011 | Ozturk et al. | |
| 2013/0261498 A1 | 10/2013 | Burdorff et al. | |
| 2013/0267870 A1 | 10/2013 | Lonky | |
| 2014/0012158 A1 | 1/2014 | Miller et al. | |
| 2014/0018699 A1 * | 1/2014 | Rusnak | A61B 10/0233 600/566 |

FOREIGN PATENT DOCUMENTS

CN         201404234 Y       2/2010

* cited by examiner

*Primary Examiner* — Michael C Stout
*Assistant Examiner* — Nicholas E Kolderman
(74) *Attorney, Agent, or Firm* — Patent Technologies, LLC; Robert D. Gunderman, Jr.

(57) ABSTRACT

An Advanced Biopsy Needle is disclosed that provides both fine needle aspiration and core biopsy with a single insertion, thus reducing trauma and pain to the patient. An inner needle for aspiration and an outer needle for core biopsy are in coaxial relation to each other, thus providing both histology and cytology functions with a single medical device and also with a single insertion. Lateral cutting edges along fenestration openings in the outer needle ensure that adequate tissue samples are taken. A syringe is attached to the inner needle for collection of aspirate.

15 Claims, 10 Drawing Sheets

ADVANCED BIOPSY NEEDLE

BACKGROUND OF THE INVENTION

1. Field of the Invention

The present invention relates generally to medical needles, and more particularly to an Advanced Biopsy Needle.

2. Description of the Related Art

Biopsy needles are commonly used to retrieve tissue, fluids, or other bodily samples for testing. Fine needle aspiration, for example, is a procedure where a needle is passed through the skin into areas of concern such as cysts, nodules, internal organs or other masses. The sample of fluids and/or cells is then aspirated through the needle into a syringe or similar collection device. The sample of cells then undergoes a cytology exam or perhaps a histology exam should tissue be collected along with the aspirated cells. Another common biopsy procedure is a core needle biopsy where a larger, hollow needle is used to remove cores of tissue from the area of concern. A core biopsy at times involves multiple insertions to ensure that adequate tissue samples are collected for a histology exam. While there are other biopsy procedures, fine needle aspiration and core needle biopsy are the most common, and at times both procedures are used on a patient.

What is therefore needed and beneficial is a biopsy needle that provides both fine needle aspiration and core biopsy with a single insertion, thus reducing trauma and pain to the patient. What is also needed is a biopsy needle that provides superior tissue retrieval and sampling with a single insertion.

It is thus an object of the present invention to provide an Advanced Biopsy Needle. While the Advanced Biopsy Needle comprises an inner and outer needle, the term Advanced Biopsy Needle refers to both needles and the novel coaxial arrangement of the inner aspiration needle and the outer core needle. These and other objects of the present invention are not to be considered comprehensive or exhaustive, but rather, exemplary of objects that may be ascertained after reading this specification with the accompanying drawings and claims.

BRIEF SUMMARY OF THE INVENTION

In accordance with the present invention, there is provided an Advanced Biopsy Needle comprising an outer needle comprising a hollow metal wire having a shaft, a sharp end, a fastening end and a cutting slot, the cutting slot comprising at least one fenestration opening having lateral walls wherein at least one lateral wall has a sharp cutting surface; an outer needle hub affixed to the fastening end of the outer needle; an inner needle comprising a hollow metal wire having a shaft, a sharp end and a fastening end; and an inner needle hub affixed to the fastening end of the inner needle; wherein the outer needle and the inner needle are arranged coaxial with each other such that the outer needle and the inner needle penetrate tissue together and wherein the inner needle can be removed from the outer needle once aspiration is performed.

The foregoing paragraph has been provided by way of introduction, and is not intended to limit the scope of the invention as described by this specification and the attached drawings and claims.

BRIEF DESCRIPTION OF THE DRAWINGS

The invention will be described by reference to the following drawings, in which like numerals refer to like elements, and in which.

The present invention will be described in connection with a preferred embodiment, however, it will be understood that there is no intent to limit the invention to the embodiment described. On the contrary, the intent is to cover all alternatives, modifications, and equivalents as may be included within the spirit and scope of the invention as defined by this specification, drawings and claims provided herein.

DESCRIPTION OF THE PREFERRED EMBODIMENTS

The Advanced Biopsy Needle of the present invention may have various embodiments, some of which are described herein, and others of which may be inferred from or otherwise envisioned based on the disclosure contained herein.

Medical needles, including those of the present invention, are generally constructed from a hollow metal wire where a shaft is formed with a sharp end and a fastening end for placement of a fastening device that is then removably connected to a syringe or the like. Stainless steel is a commonly used material for medical needles. To manufacture a medical needle, the hollow metal wire, or cannula, is formed from a larger metal tube which is fabricated by rolling a sheet of metal into a tube and then welding the resulting seam. Laser welding is commonly used to join the tube together. Another technique to create a medical needle is where a solid piece of metal may be bored and machined, however such an approach is significantly more costly than welding a formed tube. Once the rolled and welded metal tube is created, it is heated and drawn through a series of progressively smaller dies to stretch the length of the tube while at the same time decrease the diameter of the tube until the final draw is performed typically without heat. Cold working of the tube increases the strength and hardness of the tube. At times a mandrel of similar form is placed inside the tube to prevent tube wall collapse, but usually the tolerances provided by the equipment and related manufacturing processes are such that a mandrel or form is not necessary. Once a hollow metal wire is created, it is cut to a specified length and a sharp end is created on a first end of the cut hollow metal wire by grinding, cutting a bevel, or the like. For the Advanced Biopsy Needle of the present invention, the outer needle then receives a secondary operation where cutting slots are formed in the wall of the needle by grinding, cutting, or the like. Lastly, with medical needles, a Luer fastener such as a LUER-LOCK® or a LUER-SLIP® connector is placed on the fastening end of the hollow metal wire by press fitting, friction fitting, adhesion, or the like. LUER-LOCK® and LUER-SLIP® are registered trademarks of Becton Dickinson and Company of Franklin Lakes, N.J.

The present invention and the various embodiments described and envisioned herein will be further described herein, with the drawings forming an essential part of the disclosure. The drawings were created using 3D modeling software, and portray exemplary, but not limiting, embodiments of the present invention.

The Advanced Biopsy Needle of the present invention allows for the extraction of both cells as well as tissue through a novel slotted sleeve and retractable core arrangement. The hollow slotted sleeve of the biopsy needle has at least one fenestration opening such as a slot in the sleeve, as well as a sharpened tip for insertion. The lateral walls of the slot are blade-sharp to facilitate cutting and sampling of tissue. The hollow slotted sleeve or outer needle is coaxial with a retractable core or inner needle, and both inserted in the anatomical area to be sampled. The hollow slotted sleeve or outer needle has a handle to facilitate rotation of the outer needle once inserted. A retractable core inner needle, also hollow and with a sharpened tip, is inserted within the sleeve or outer needle to prevent passageway tissue(s) from collapsing into the hollow slotted sleeve or outer needle. Once the desired target tissue is reached, the inner needle retractable core is used to aspirate cells for cytology examination and/or fluids. The inner needle retractable core is then withdrawn, while the hollow slotted sleeve outer needle is left in place for the desired tissue sample retrieval. Tissue sample is then obtained by rotation of the hollow slotted sleeve outer needle. Upon removal of the hollow slotted sleeve outer needle, the tissue sample is captured and can be extracted for subsequent testing and analysis.

Two exemplary embodiments of the Advanced Biopsy Needle are depicted by way of example and depicted with the attached figures. Both embodiments have two cutting slots with differing placement along the axis of the outer needle. In some embodiments of the present invention, one cutting slot or more than two cutting slots are employed. In describing the present invention and the various embodiments described and envisioned herein, the term axis is used. The axis of each needle is parallel with the length of the needle, in other words the axis follows the open inner passageway of the needle.

Figure 1:
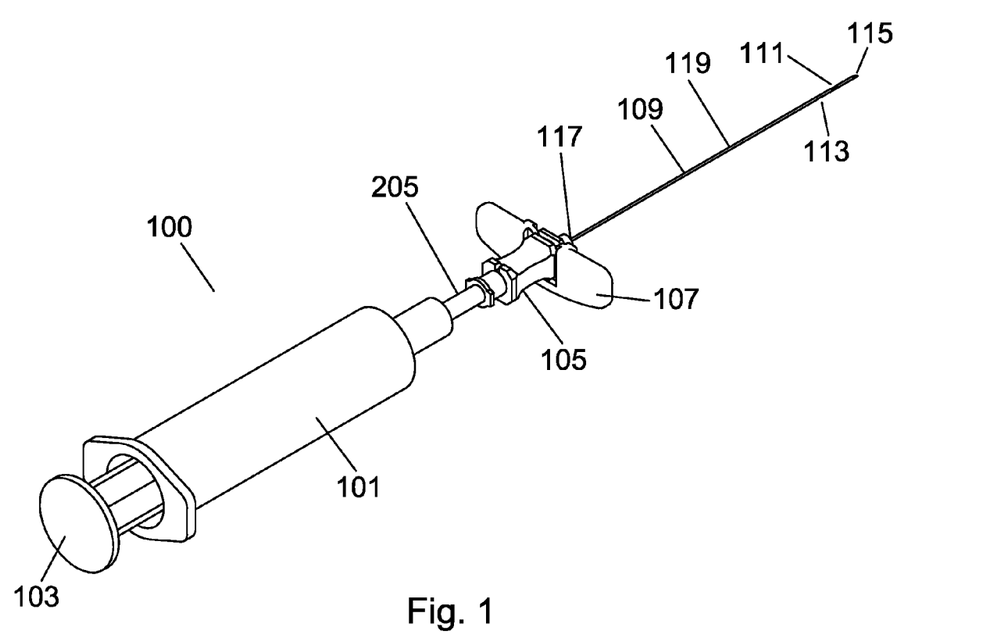
FIG. 1 depicts a perspective view of the Advanced Biopsy Needle.
Figure 2:
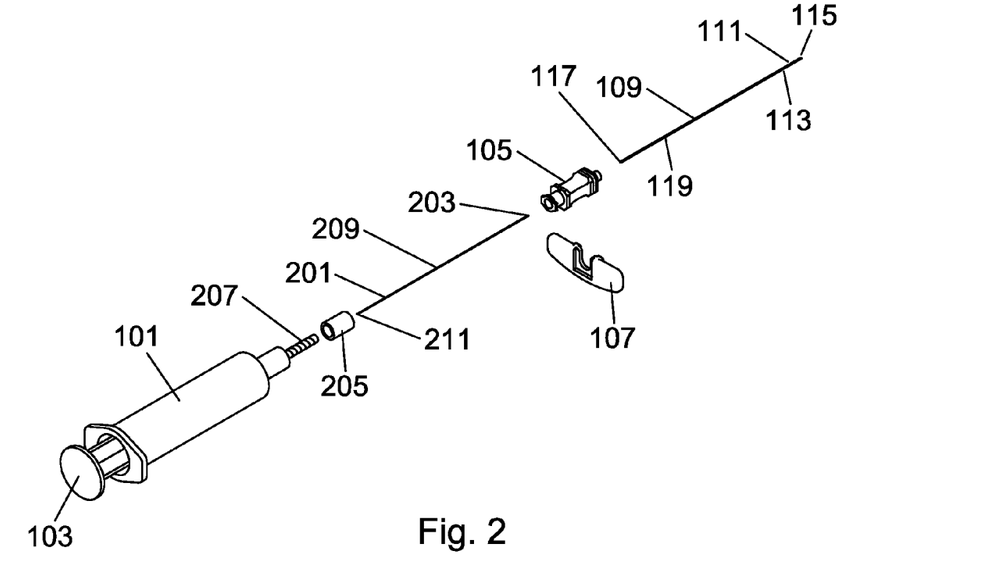
FIG. 2 is an exploded view of the Advanced Biopsy Needle of FIG. 1.

Turning now to the various figures provided, FIG. 1 depicts a perspective view of the Advanced Biopsy Needle 100. The inner needle and outer needle are assembled in coaxial relation to each other, and the inner needle cannot be seen in FIG. 1. The outer needle 109 can be seen with a first cutting slot 111 and a second cutting slot 113. Each of these fenestration openings will be depicted in further detail in subsequent figures. The outer needle 109 has a shaft 119 with a sharp end or outer needle tip 115 and a fastening end 117. The sharp end or outer needle tip 115 may be provided with a bevel or similar sharpened feature for ease of insertion into bodily tissue. The fastening end 117 receives an outer needle hub 105 that may include, in some embodiments of the present invention, a Luer fastener or the like. The outer needle hub may also include, in some embodiments of the present invention, a grip 107 such as a pair of outwardly extending wings, a lever, a knurled surface, a textured surface, a cylindrical surface, a rectangular extension, a triangular extension, a curved or non-linear surface, or the like. The outer needle hub 105 and related grip 107 may be made from a plastic such as nylon, polypropylene, or the like, and may be made by injection molding, blow molding, printing, machining, or the like. Fastened to the outer needle 109 by way of the outer needle hub 105 and related fastener is a syringe 101 that comprises a barrel (body of the syringe as indicated by 101) and a plunger 103. The syringe may be made from a plastic such as, for example, polypropylene, nylon, and may be made by injection molding, blow molding, printing, machining, or the like, or may be made from other material such as glass, metal, or the like. The plunger 103 may include a sealing tip made from silicone, a rubber, or the like, in order to push or pull fluid in or out of the syringe barrel. The plunger 103 and barrel 101 (syringe) may also be made from a plastic such as, for example, polypropylene, nylon, and may be made by injection molding, blow molding, printing, machining, or the like, or may be made from other material such as glass, metal, or the like. Also shown in FIG. 1, and depicted in more detail in FIG. 2, is an inner needle hub 205 that is fastened to a fastening end of the inner needle (not shown in FIG. 1, see FIG. 2). The inner needle hub 205 may be made from a plastic such as polypropylene or nylon, and may be made by injection molding, blow molding, printing, machining, or the like.

FIG. 2 is an exploded view of the Advanced Biopsy Needle of FIG. 1. The inner needle 201 can be clearly seen with an inner needle tip or sharp end 203, a shaft 209, a fastening end 211 with an inner needle hub 205 attached thereto. A syringe hub 207 can also be seen for removable coupling of the inner needle 201 to the syringe 101. The inner needle hub 205 may be made from a plastic such as, for example, polypropylene, nylon, and may be made by injection molding, blow molding, printing, machining, or the like, or may be made from other material such as metal, or the like. The inner needle hub 205 may also include a fastener such as a Luer fastener or the like. The inner needle hub 205 removably attaches to the syringe hub 207. Further, in some embodiments of the present invention, the inner needle hub 205 fits at least partially within the outer needle hub 105 or further mates together. In some embodiments of the present invention, the inner needle hub 205 and the outer needle hub 105 contain mating surfaces such that each hub receives and couples with the other. Such mating surfaces may contain ridges, valleys, locking features, or the like. In one embodiment of the present invention, the inner needle tip 203 and the outer needle tip 115 are in alignment with each other when initially installed in coaxial relation one to the other. In some embodiments of the present invention, guides, tabs, slots, or other features may be employed to ensure that the inner needle tip 203 and the outer needle tip 115 stay in alignment with each other.

Figure 3:
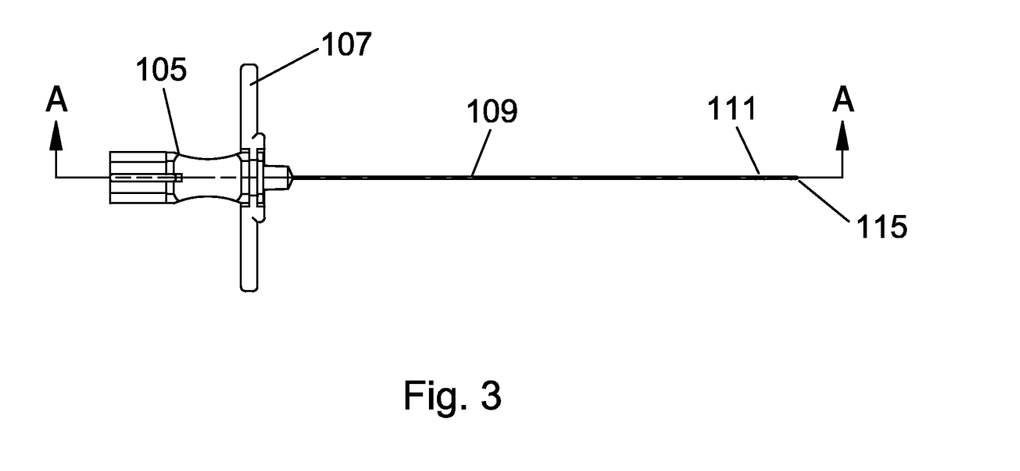
FIG. 3 is a plan view of the Advanced Biopsy Needle.
Figure 4:
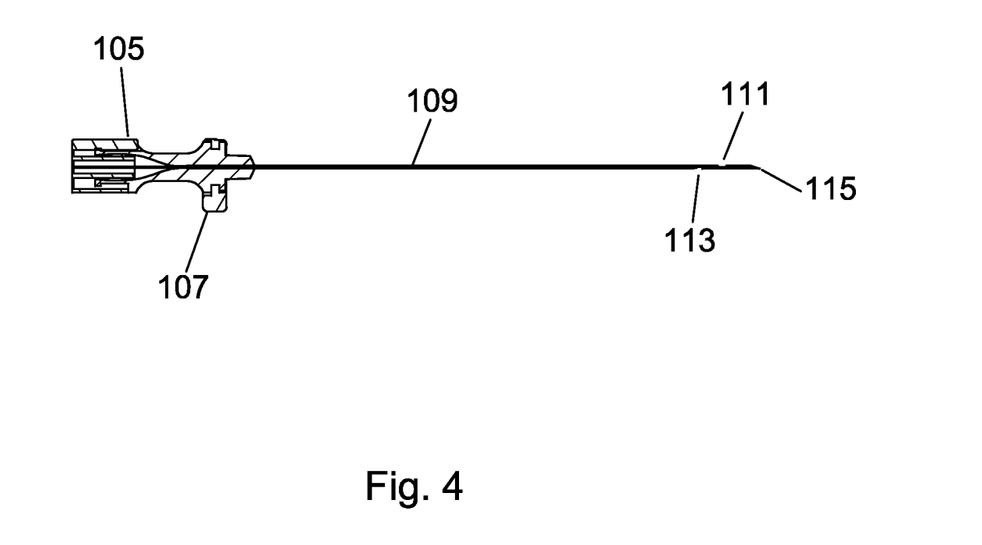
FIG. 4 is a cross sectional view of the Advanced Biopsy Needle taken along line A-A of FIG. 3.
Figure 5:
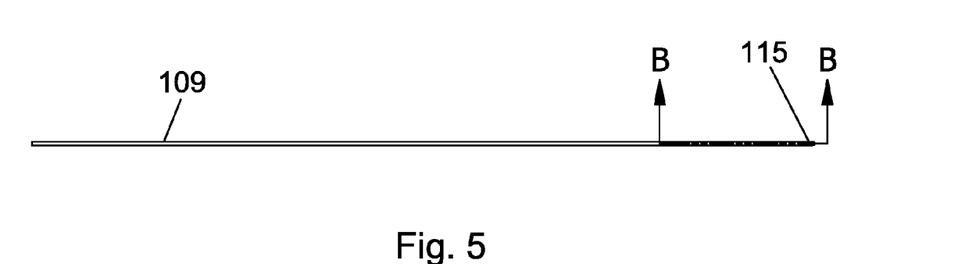
FIG. 5 is a plan view of the outer needle of the Advanced Biopsy Needle of FIG. 1.
Figures 6, 7:
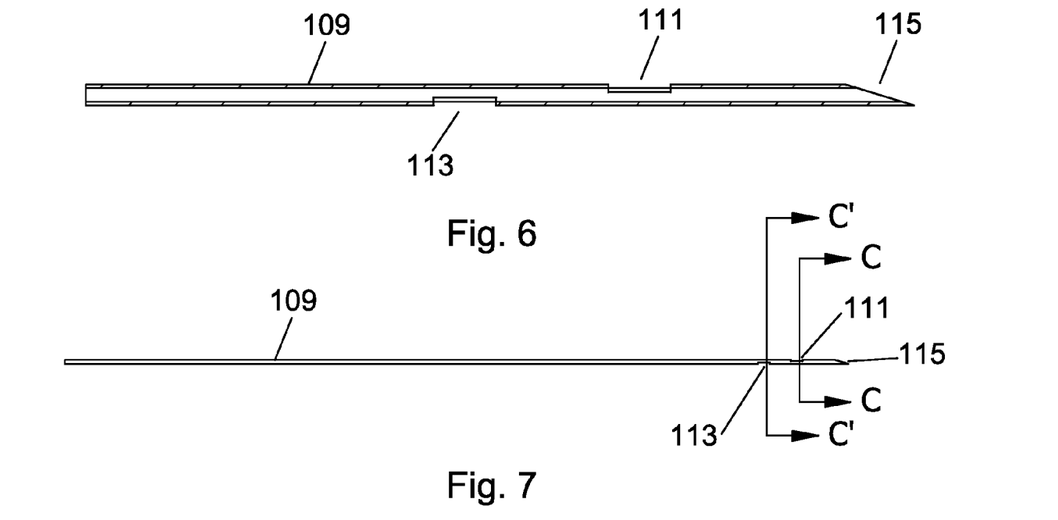
FIG. 6 is a close up cross sectional view of the outer needle of FIG. 5 taken along line B-B of FIG. 5.
FIG. 7 is a plan view of the outer needle of the Advanced Biopsy Needle of FIG. 1.
Figure 8A:
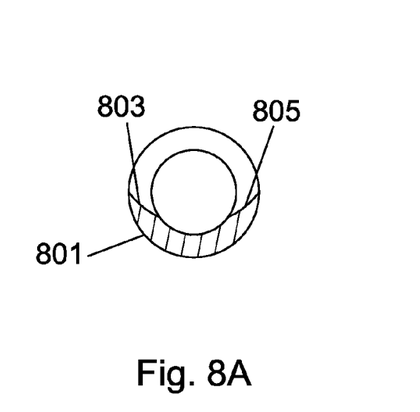
FIG. 8A is a cross sectional view of the outer needle taken along line C'-C' of FIG. 7.
Figure 8B:
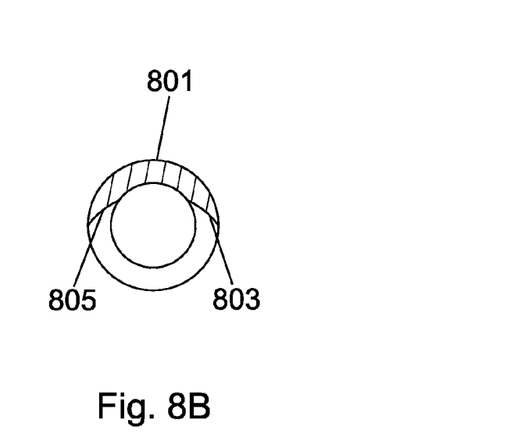
FIG. 8B is a cross sectional view of the outer needle taken along line C-C of FIG. 7.

FIG. 3 is a plan view of the Advanced Biopsy Needle showing the outer needle 109 and an exemplary needle hub 105 that has been fitted with a grip 107. FIG. 4 is a cross sectional view of the Advanced Biopsy Needle taken along line A-A of FIG. 3 so that the first cutting slot 111 and the second cutting slot 113 are clearly depicted. The first and second cutting slots are depicted as rectangular fenestration openings; however, other geometries such as square openings, oval openings, circular openings, and the like may also be employed. In addition, variation of needle size, fenestration to tip spacing, slot to slot spacing, direction of slots, percent of total circumference of the needle removed or remaining for each slot, and other dimensional attributes are to be considered within the scope and content of the present invention. Such changes may be made for a variety of reasons, including but not limited to, the tissue to be biopsied. FIG. 5 is a plan view of the outer needle 109 of the Advanced Biopsy Needle of FIG. 1 without an outer needle hub attached. To more clearly see an example of a first cutting slot 111 and a second cutting slot 113, FIG. 6 is a close up cross sectional view of the outer needle of FIG. 5 taken along line B-B of FIG. 5. Each fenestration opening has two lateral walls where at least one lateral wall has a sharp cutting surface. The lateral walls are essentially the perimeter or edge of the fenestration opening that is generally parallel to the axis of the outer needle 109. To create a sharp cutting surface along a lateral wall, a bevel or taper is created by grinding, machining, cutting or the like. FIG. 7 is a plan view of the outer needle of the Advanced Biopsy Needle of FIG. 1 that depicts one embodiment of the fenestration openings. For a better understanding of the sharp cutting surface of each cutting slot, FIG. 8 is a cross sectional view of the outer needle taken along line C-C of FIG. 7. Since a portion of the perimeter of the outer needle wall has been removed in order to create each fenestration opening, a lateral section 801 has been created where the wall of the outer needle does not span the entire perimeter of the outer needle, as seen in FIG. 8. This lateral section 801 in turn has two lateral walls, each of which in one embodiment have been sharpened to create a first cutting edge lateral wall 803 and a second cutting edge lateral wall 805. In one embodiment of the present invention, the cutting edge of each lateral wall is tapered inwardly.

Figure 9:
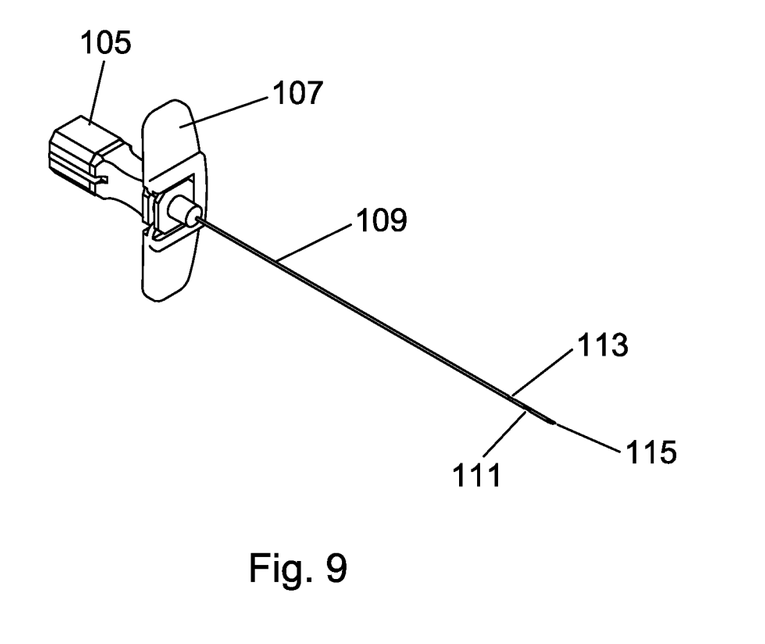
FIG. 9 is a perspective view of the Advanced Biopsy Needle without an attached syringe.

FIG. 9 is a perspective view of the Advanced Biopsy Needle without an attached syringe and with only the outer needle 109 visible.

Figure 10:
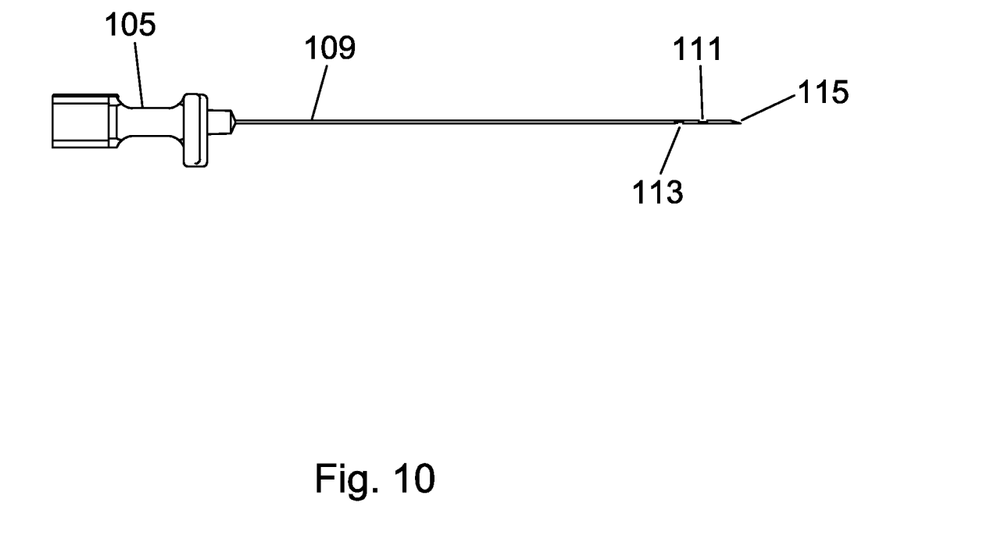
FIG. 10 is a rotated plan view of the Advanced Biopsy Needle.

FIG. 10 is a rotated plan view of the Advanced Biopsy Needle showing the first cutting slot 111 and the second cutting slot 113. It should be noted that the placement of the cutting slots, and the quantity thereof, may vary. A change in placement of each cutting slot along the axis of the outer needle provides for tissue sampling at varying depths of penetration, which may prove useful for various procedures.

Figure 11:
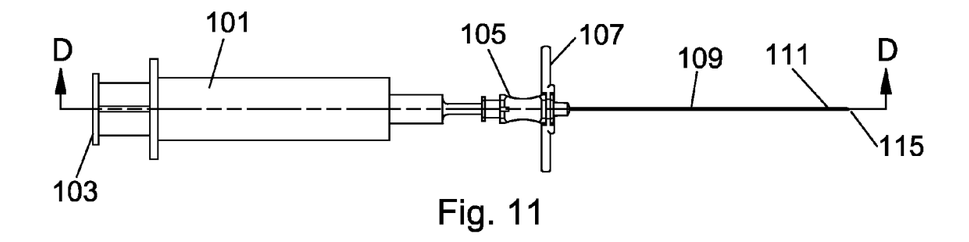
FIG. 11 is a plan view of the Advanced Biopsy Needle with an attached syringe.
Figure 12:
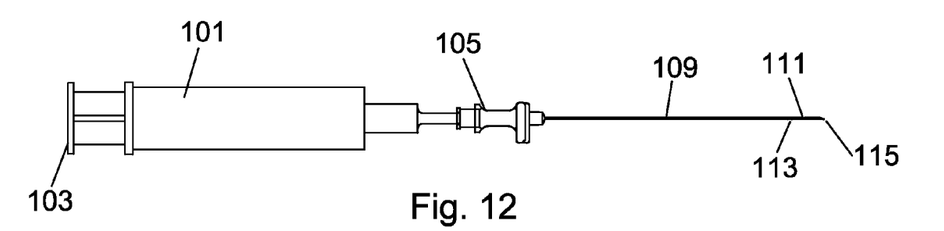
FIG. 12 is a rotated plan view of the Advanced Biopsy Needle with an attached syringe.
Figure 13:
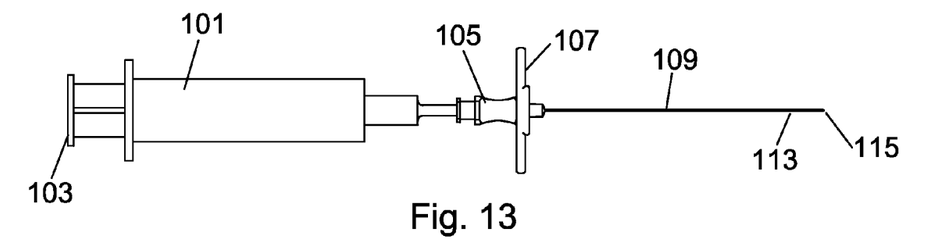
FIG. 13 is a further rotated plan view of the Advanced Biopsy Needle with an attached syringe.
Figure 14:
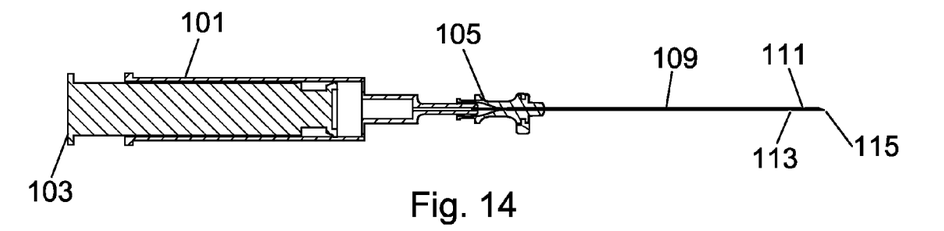
FIG. 14 is a cross sectional view of the Advanced Biopsy Needle taken along line D-D of FIG. 11.

FIG. 11 is a plan view of the Advanced Biopsy Needle with an attached syringe showing an exemplary embodiment of the visible outer needle 109. The inner needle cannot be seen. FIG. 12 is a rotated plan view of the Advanced Biopsy Needle with an attached syringe. FIG. 13 is a further rotated plan view of the Advanced Biopsy Needle with an attached syringe. FIG. 14 is a cross sectional view of the Advanced Biopsy Needle taken along line D-D of FIG. 11. In FIG. 14, the inner workings of the syringe 101 can be seen including the plunger 103 and sealing end that traverses the interior of the syringe barrel in order to maintain a seal and associated pressure or suction thereof.

Figure 15:
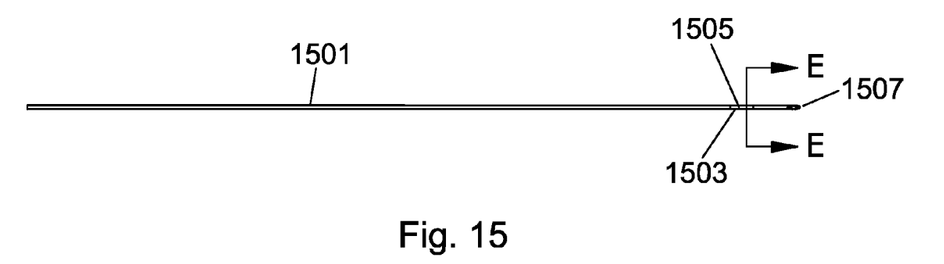
FIG. 15 is a plan view of a second embodiment of the outer needle of the Advanced Biopsy Needle.
Figure 16:
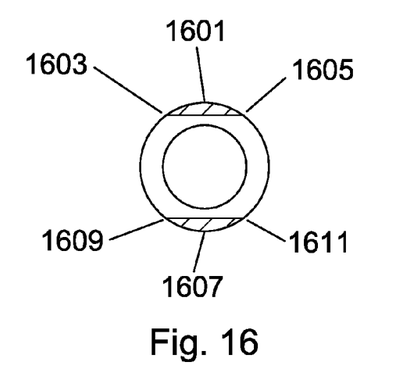
FIG. 16 is a cross sectional view of the outer needle of the Advanced Biopsy Needle taken along line E-E of FIG. 15.

As previously stated, the cutting slot fenestrations may vary in shape, position, and quantity. FIGS. 15-21 provide a second example of an embodiment of the outer needle. In the example provided by FIGS. 15-21, there are two fenestration openings opposing each other along the axis of the outer needle. FIG. 15 depicts a plan view of this second embodiment of the outer needle of the Advanced Biopsy Needle showing the second embodiment of the outer needle 1501. The outer needle comprises a first cutting slot 1503 and a second cutting slot 1505 where the two fenestration openings of each cutting slot oppose each other along the axis of the outer needle. The outer needle tip 1507 is also depicted in this example as a bevel. This will become clear upon reviewing FIGS. 16 and 17 where FIG. 16 is a cross sectional view of the outer needle of the Advanced Biopsy Needle taken along line E-E of FIG. 15. A first lateral section 1601 and a second lateral section 1607 can be seen in cross section where a first cutting edge 1603 and a second cutting edge 1605 are formed at the edge or along a contour or geometry of the first lateral section 1601. In a similar manner, a third cutting edge 1609 and a fourth cutting edge 1605 are formed at the edge or along a contour or geometry of the second lateral section 1607. These lateral sections each have two lateral walls, each of which in one embodiment have been sharpened to create the corresponding cutting edges referred to above. In one embodiment of the present invention, the cutting edge of each lateral wall is tapered inwardly.

Figure 17:
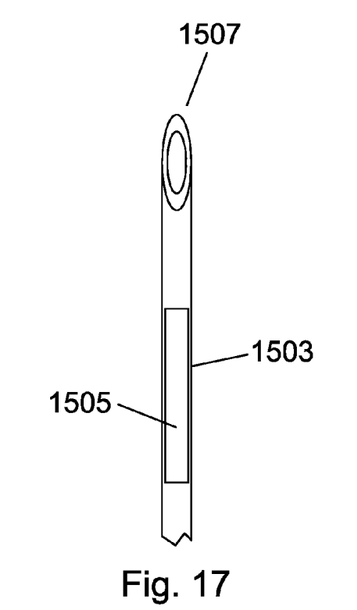
FIG. 17 is a close-up plan view of the outer needle of the Advanced Biopsy Needle of FIG. 15.

FIG. 17 is a close-up plan view of the outer needle of the Advanced Biopsy Needle of FIG. 15 which clearly shows the second cutting slot 1505 with the first cutting slot 1503 in opposing spatial relation to the second cutting slot 1505.

Figure 18:
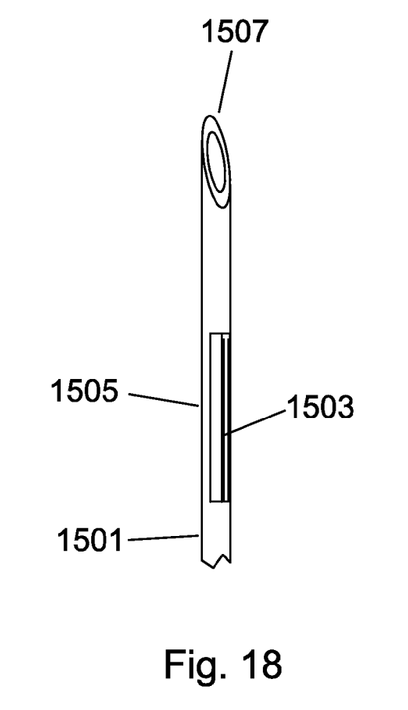
FIG. 18 is a rotated close-up plan view of the outer needle of the Advanced Biopsy Needle of FIG. 15.
Figure 19:
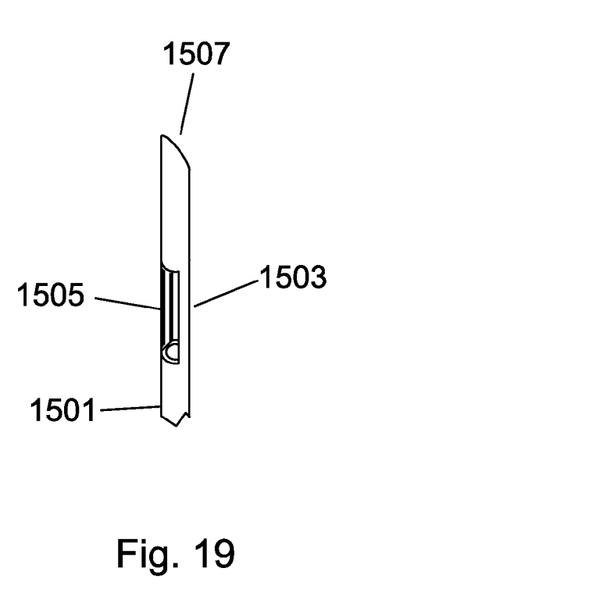
FIG. 19 is a further rotated close-up plan view of the outer needle of the Advanced Biopsy Needle of FIG. 15.
Figure 20:
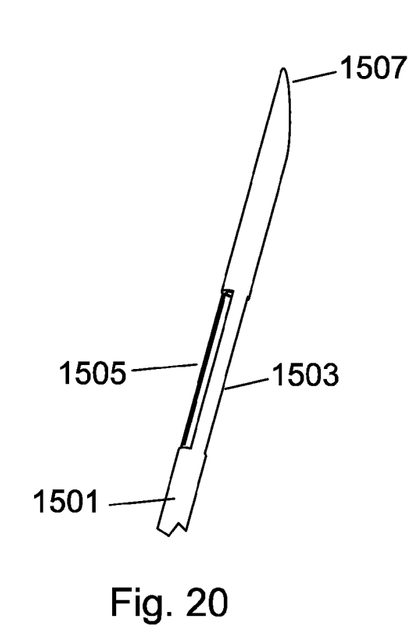
FIG. 20 is a perspective view of the outer needle of the Advanced Biopsy Needle of FIG. 15.
Figure 21:
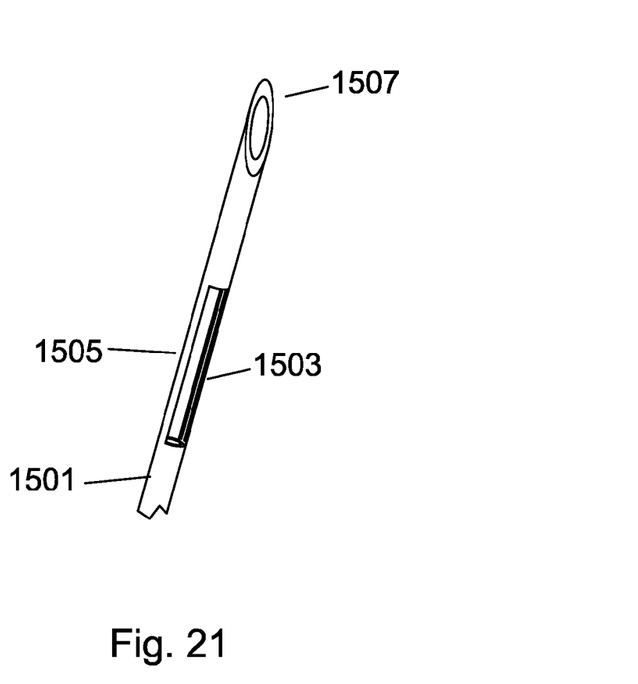
FIG. 21 is a rotated perspective view of the outer needle of the Advanced Biopsy Needle of FIG. 15.

FIG. 18 is a rotated close-up plan view of the outer needle of the Advanced Biopsy Needle of FIG. 15. FIG. 19 is a further rotated close-up plan view of the outer needle of the Advanced Biopsy Needle of FIG. 15. FIG. 20 is a perspective view of the outer needle of the Advanced Biopsy Needle of FIG. 15. FIG. 21 is a rotated perspective view of the outer needle of the Advanced Biopsy Needle of FIG. 15. In one embodiment of the present invention, the angle of the outer needle tip is in alignment with an opening in a cutting slot. In other words, when viewed from the side of the outer needle (a plan view) where the bevel of the outer needle tip is oriented such that the interior of the needle can be seen, the cutting slots will also be oriented such that there is maximum visibility through the needle from one side to the other. This alignment and orientation can be clearly seen by way of FIG. 21.

Figures 22, 23, 24:
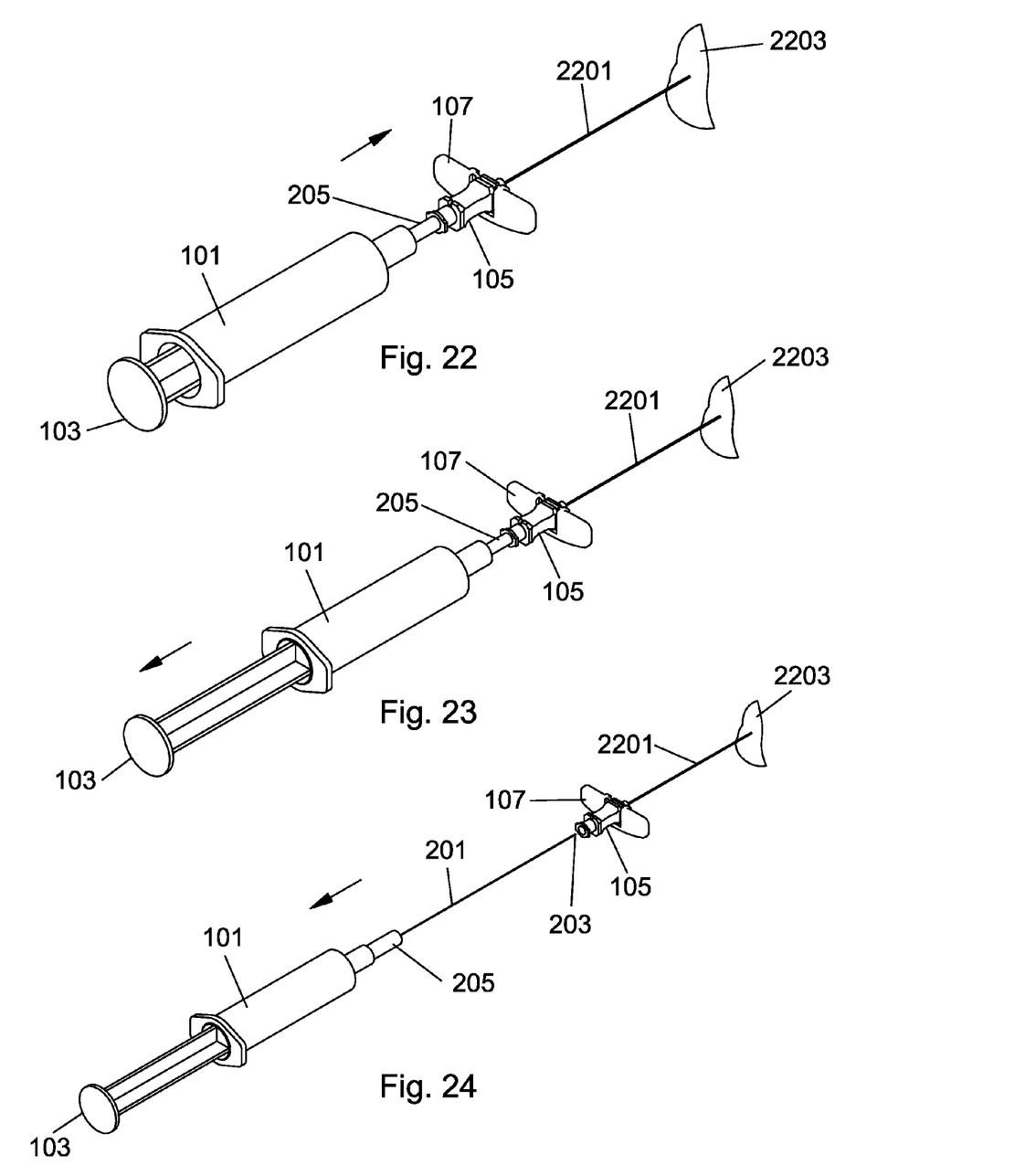
FIGS. 22-26 depict the Advanced Biopsy Needle in use for fine aspiration and core biopsy.
Figure 25:
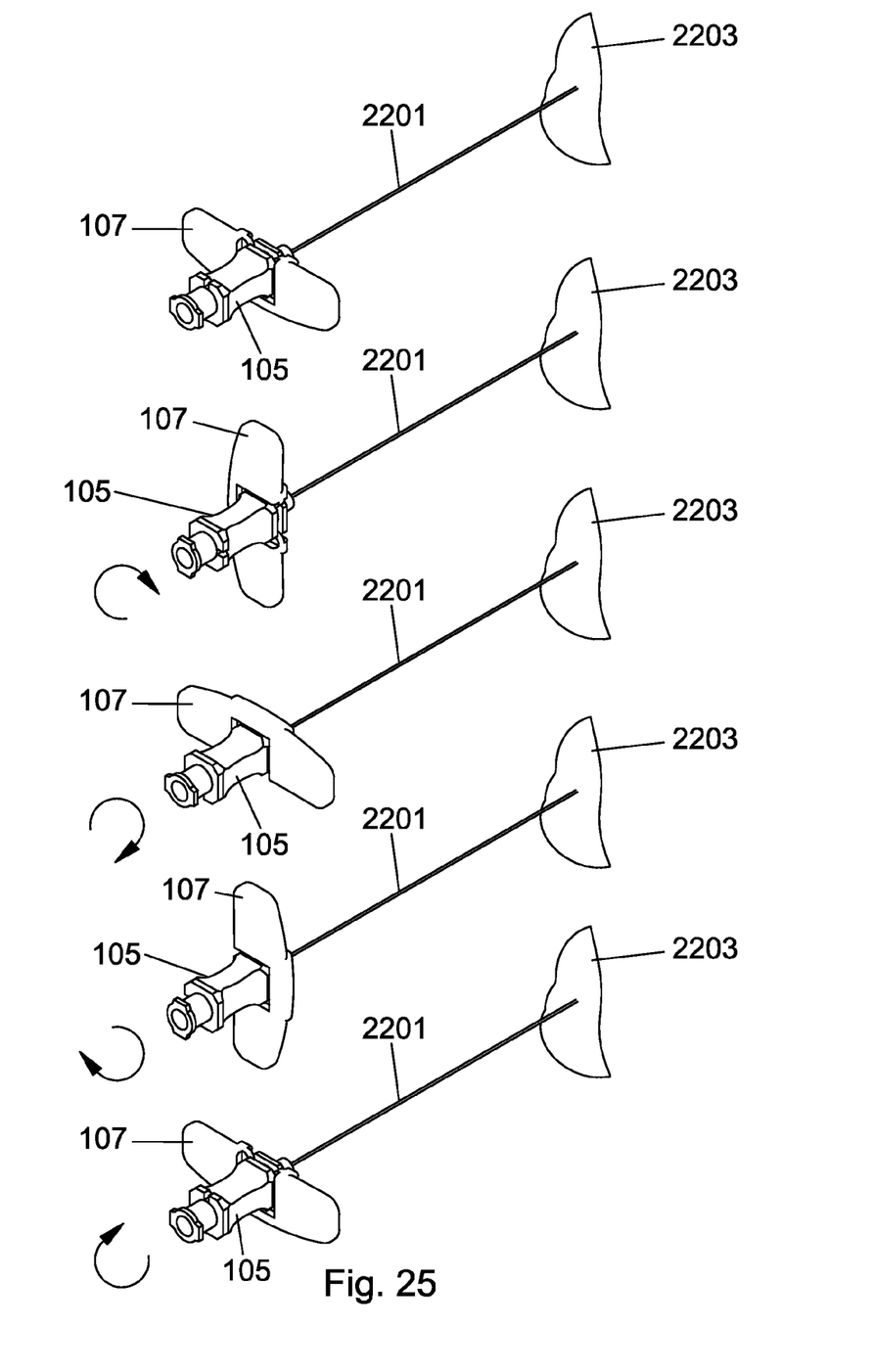
Figure 26:
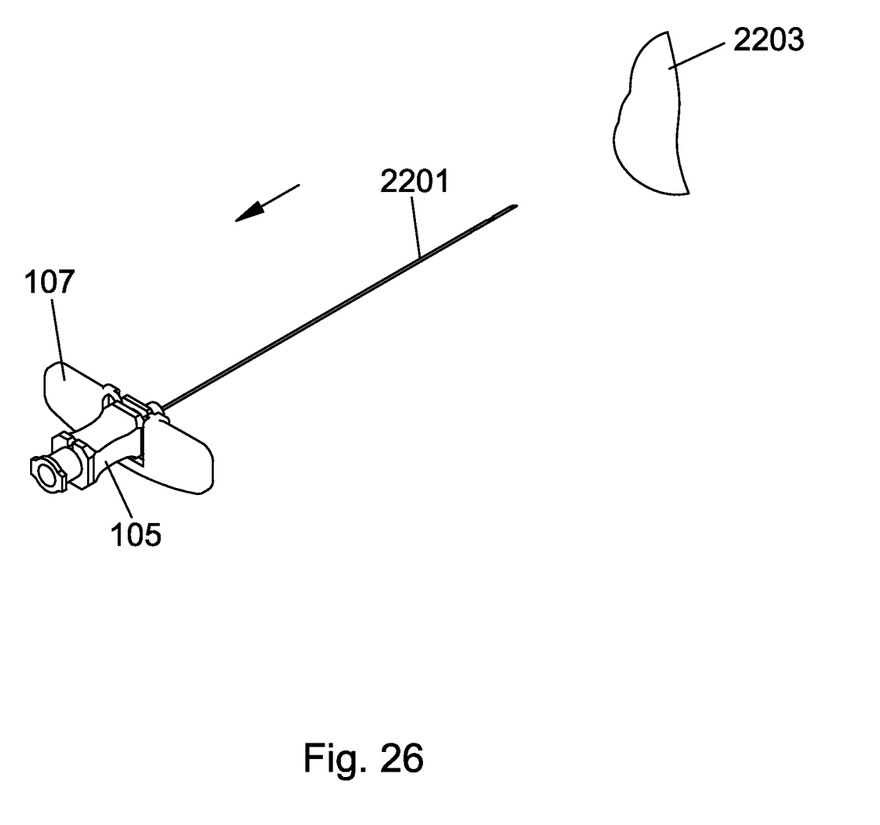

Lastly, FIGS. 22-26 sequentially depict the Advanced Biopsy Needle in use for fine aspiration and core biopsy. FIG. 22 depicts the Advanced Biopsy Needle being inserted into tissue 2203 in the direction of travel indicated by the accompanying arrow. The outer needle 2201 (any of the embodiments described or envisioned herein) can be seen being inserted in the tissue 2203 along with a (not visible) inner needle such as the inner needle 201 of FIG. 2. In FIG. 23 the plunger 103 of the syringe 101 is withdrawn to draw (aspirate) fluid and perhaps tissue into the barrel of the syringe by way of the inner needle 201 (see FIG. 2) that is connected to the syringe 101 by way of inner needle hub 205. The plunger 103 is withdrawn in accordance with the arrow that accompanies FIG. 22. In FIG. 24, the aspirated sample has been collected and the syringe 101 and attached inner needle 201 are withdrawn from the outer needle 2201, leaving the outer needle 2201 remaining in the tissue. The obtained sample can then be sent for appropriate analytical tests. FIG. 25 then depicts a series of illustrations where the outer needle 2201 is rotated using the grip 107 while remaining in the tissue 2203 such that a core sample of tissue is obtained by way of the inserted and embedded cutting slots of the outer needle 2201. Once the rotation is completed, the outer needle 2201 is withdrawn from the tissue 2203 as depicted by way of FIG. 26 and the associated directional arrow. The outer needle 2201 is then placed in a suitable sample receiving device where it can be sent for appropriate analytical tests.

It is, therefore, apparent that there has been provided, in accordance with the various objects of the present invention, an Advanced Biopsy Needle.

While the various objects of this invention have been described in conjunction with preferred embodiments thereof, it is evident that many alternatives, modifications, and variations will be apparent to those skilled in the art. Accordingly, it is intended to embrace all such alternatives, modifications and variations that fall within the spirit and broad scope of this specification, drawings, and claims provided herein.

What is claimed is:

1. An Advanced Biopsy Needle comprising:
    an outer needle comprising a hollow metal wire having a shaft, a sharp end, a fastening end, a first cutting slot and a second cutting slot, each cutting slot comprising a fenestration opening having lateral walls wherein at least one lateral wall has a sharp cutting surface;
    the at least one lateral wall of each cutting slot being generally parallel to the axis of the outer needle to remove tissue at a specific needle insertion depth when the outer needle is rotated;
    an outer needle hub affixed to the fastening end of the outer needle;
    an inner needle comprising a hollow metal wire having a shaft, a sharp end and a fastening end; and
    an inner needle hub affixed to the fastening end of the inner needle;
    wherein the outer needle and the inner needle are arranged coaxial with each other such that the outer needle and the inner needle penetrate tissue together and wherein the inner needle can be removed from the outer needle once inner needle fluidic cellular aspiration is performed;
    the sharp end of the hollow metal wire of the inner needle being configured to pass through the sharp end of the hollow metal wire of the outer needle when the outer needle and the inner needle are arranged coaxial with each other to allow for inner needle fluidic cellular aspiration with the outer needle in place; and
    wherein the inner needle prevents tissue from entering the cutting slots of the outer needle until a specific needle insertion depth is achieved and the inner needle is then removed from the outer needle.

2. The Advanced Biopsy Needle of claim 1, wherein the inner needle hub further comprises a Luer fitting for releasably mounting the inner needle to a syringe.

3. The Advanced Biopsy Needle of claim 1, wherein the inner needle hub fits at least partially within the outer needle hub.

4. The Advanced Biopsy Needle of claim 1, wherein the inner needle hub and the outer needle hub mate together.

5. The Advanced Biopsy Needle of claim 1, further comprising a grip attached to the outer needle hub.

6. The Advanced Biopsy Needle of claim 5, wherein the grip further comprises a pair of outwardly extending wings.

7. The Advanced Biopsy Needle of claim 5, wherein the grip is removable.

8. The Advanced Biopsy Needle of claim 6, wherein the pair of outwardly extending wings is removable.

9. The Advanced Biopsy Needle of claim 1, wherein the first cutting slot and the second cutting slot are opposing each other along the axis of the outer needle.

10. The Advanced Biopsy Needle of claim 1, further comprising a syringe removably attached to the inner needle hub.

11. The Advanced Biopsy Needle of claim 10, wherein the syringe is removably attached to the inner needle hub with a Luer fitting.

12. An Advanced Biopsy Needle comprising:
    an outer needle comprising a hollow metal wire having a shaft, a sharp end, a fastening end, a first cutting slot and a second cutting slot, each cutting slot comprising a fenestration opening having lateral walls wherein at least one lateral wall has a sharp cutting surface;
    the at least one lateral wall of each cutting slot being generally parallel to the axis of the outer needle to remove tissue at a specific needle insertion depth when the outer needle is rotated;
    an outer needle hub affixed to the fastening end of the outer needle;
    an inner needle comprising a hollow metal wire having a shaft, a sharp end and a fastening end;
    an inner needle hub affixed to the fastening end of the inner needle; and
    a syringe removably attached to the inner needle hub;
    wherein the outer needle and the inner needle are arranged coaxial with each other such that the outer needle and the inner needle penetrate tissue together and wherein the inner needle can be removed from the outer needle once inner needle fluidic cellular aspiration is performed;
    the sharp end of the hollow metal wire of the inner needle being configured to pass through the sharp end of the hollow metal wire of the outer needle when the outer needle and the inner needle are arranged coaxial with each other to allow for inner needle fluidic cellular aspiration with the outer needle in place; and
    wherein the inner needle prevents tissue from entering the cutting slots of the outer needle until a specific needle insertion depth is achieved and the inner needle is then removed from the outer needle.

13. The Advanced Biopsy Needle of claim 12, wherein the first cutting slot and the second cutting slot are opposing each other along the axis of the outer needle.

14. An Advanced Biopsy Needle comprising:
    an outer needle comprising a hollow metal wire having a shaft, a sharp end, a fastening end, a first cutting slot and a second cutting slot, each cutting slot comprising a fenestration opening having lateral walls wherein at least one lateral wall has a sharp cutting surface;
    the at least one lateral wall of each cutting slot being generally parallel to the axis of the outer needle to remove tissue at a specific needle insertion depth when the outer needle is rotated;
    an outer needle hub affixed to the fastening end of the outer needle;

an inner needle comprising a hollow metal wire having a shaft, a penetrating end and a fastening end;

an inner needle hub affixed to the fastening end of the inner needle; and a syringe removably attached to the inner needle hub;

wherein the outer needle and the inner needle are arranged coaxial with each other such that the outer needle and the inner needle penetrate tissue together and wherein the inner needle can be removed from the outer needle once inner needle fluidic cellular aspiration is performed;

the sharp end of the hollow metal wire of the inner needle being configured to pass through the sharp end of the hollow metal wire of the outer needle when the outer needle and the inner needle are arranged coaxial with each other to allow for inner needle fluidic cellular aspiration with the outer needle in place; and wherein the inner needle prevents tissue from entering the cutting slots of the outer needle until a specific needle insertion depth is achieved and the inner needle is then removed from the outer needle.

15. The Advanced Biopsy Needle of claim 14, wherein each cutting slot is generally rectangular.

* * * * *